US00PP17826P2

(12) United States Plant Patent
Zaiger et al.

(10) Patent No.: US PP17,826 P2
(45) Date of Patent: Jun. 26, 2007

(54) INTERSPECIFIC TREE NAMED 'BELLA GOLD'

(50) Latin Name: ***Prunus* species**
Varietal Denomination: Bella Gold

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 27 days.

(21) Appl. No.: 11/320,296

(22) Filed: Dec. 29, 2005

(51) Int. Cl.
*A01H 5/00* (2006.01)

(52) U.S. Cl. ..... Plt./180
(58) Field of Classification Search ..... Plt./180, Plt./186
See application file for complete search history.

*Primary Examiner*—Kent Bell
*Assistant Examiner*—Annette H Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and productive bearer of fruit.
2. Fruit with very good flavor and eating quality.
3. Fruit with an attractive orange red skin blush.
4. Having firmer flesh than most commercial apricots.
5. Fruit holding firm on the tree 8 to 10 days after maturity (shipping ripe).
6. Relatively uniform ripening of fruit throughout the tree.

1 Drawing Sheet

Botanical classification: Interspecific *Prunus* species.

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, are 'Geo Pride' (U.S. Plant Pat. No. 10,386), 'Flavor Queen' (U.S. Plant Pat. No. 7,420) and the proprietary interspecific tree '38GH47'.

ORIGIN OF THE VARIETY

The new and distinct variety of interspecific tree, a combination of crosses between (*Prunus salicina* and *Prunus armeniaca*) was originated by us in our experimental orchard located near Modesto, Calif. from seed collected from an open pollinated interspecific proprietary selection with field identification number '38GH47'. We originated the interspecific tree (38GH47) from a cross between the interspecific 'Geo Pride' (U.S. Plant Pat. No. 10,386), the maternal parent and the interspecific 'Flavor Queen' (U.S. Plant Pat. No. 7,420), the pollen parent. A large number of these open pollinated seedlings were planted on their own root system, under close observation, one such seedling exhibited desirable fruit characteristics and was selected in 1997 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree, [(Plum×Plumcots)× Unknown pollen], has these characteristics, (pubescent skin and apricot flesh texture) that indicate the paternal parent may be from apricot pollen. The new variety is large, semi-vigorous, has a spreading growth habit and is a regular and productive bearer of medium size, semi-freestone fruit with very good flavor and eating quality. The fruit is further characterized by having skin with a bright yellow ground color with an attractive orange red blush covering approximately 30% of the skin, having firm flesh and holding firm on the tree 8 to 10 days after maturity, (shipping ripe). The fruit having good handling, storage and shipping quality, with an average Brix of 15.7°. In comparison to its maternal interspecific parent (38GH47), the new variety has pubescence similar to an apricot, compared to smooth skin, similar to a plum and is approximately 24 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 7 years of age, its flowers, foliage and fruit, as based on observations of 7 year old specimens grown near Modesto, Calif., with color in accordance with Munsell Book of Color.

Tree:

*Size.*—Large, pruned in height to 3 to 3.5 meters for economical harvesting of fruit. Average spread 3 meters, varies with different cultural practices.

*Vigor.*—Semi-vigorous, tree growth of 1.2 to 1.5 meters in height the first growing season, varies with soil type, fertility and cultural practices.

*Form.*—Spreading. Crotch angle approximately 40°, increases with heavy crop load.

*Branching habit.*—Spreading, usually pruned to vase shape to allow more sunlight and air movement to center of tree to enhance health of fruit spurs and fruit color.

*Productivity.*—Productive, fruit thinning and spacing necessary to enhance desired market size fruit. Varies with climatic conditions during blooming period.

*Bearer.*—Regular, 4 consecutive years of adequate fruit set, no alternate bearing observed.

*Fertility.*—Self sterile, pollinator required.

*Density.*—Medium dense, pruned to vase shape to allow for sunlight and air penetration.

*Hardiness.*—Hardy in all stone fruit growing areas of California. Tree grown in USDA Hardiness Zone 9. Winter chilling requirement approximately 600 hours at or below 45° F.

Trunk:

*Size.*—Large. Average circumference 50.8 cm at 30.4 cm above ground on a 7 year old tree.

*Stocky.*—Medium stocky.

*Texture.*—Medium shaggy, increases with age of tree.

*Color.*—Varies from 5Y 4/2 to 5Y 5/2.

Branches:

*Size.*—Medium. Average circumference 16.0 cm at 1.2 meters above ground.

*Surface texture.*—New growth relatively smooth. Mature growth medium rough.

*Lenticels.*—Average number of 47 in a 25.8 square cm surface area. Size — small to medium. Average length 3.1 mm. Average width 0.9 mm. Color varies from 10YR 6/8 to 10YR 5/8.

*Color.*—New growth varies from 2.5GY 7/8 to 10Y 5/6. Mature growth varies from 7.5YR 3/4 to 7.5Y 4/4, varies with age of growth.

Leaves:

*Size.*—Medium to large. Average length 83.0 mm. Average width 50.3 mm.

*Form.*—Elliptic.

*Apex.*—Cuspidate.

*Base.*—Obtuse.

*Margin.*—Serrulate.

*Thickness.*—Medium.

*Surface texture.*—Upper surface relatively smooth, slightly indented over midrib and leaf veins. Lower surface relatively smooth, small ridges created by midrib and pinnate venation. Both surfaces glabrous.

*Petiole.*—Average length 19.7 mm. Average width 1.3 mm. Longitudinally grooved. Surface — glabrous. Color varies 2.5GY 7/6 to 5R 5/10, darkens where exposed to sun.

*Glands.*—Size — small to medium. Average length 0.7 mm. Average width 0.6 mm. Type — globose. Average number 2, varies from 1 to 3. Located primarily on upper portion of petiole and base of leaf blade. Color varies from 2.5GY 6/6 to 5GY 5/6.

*Color.*—Upper surface varies from 5GY 4/6 to 5GY 3/6. Lower surface varies from 5GY 5/4 to 5GY 5/6. Midvein color varies from 5GY 7/4 to 5GY 8/4.

Flower buds:

*Size.*—Medium. Average length 13.3 mm. Average diameter 8.0 mm.

*Hardiness.*—Hardy in all stone fruit growing areas of California.

*Form.*—Conical, becoming slightly elongated just before opening.

*Pedicel.*—Short. Average length 3.3 mm. Average width 0.9 mm. Color varies from 5GY 8/6 to 5GY 7.6.

*Color.*—N9.5/ (white), some buds with very slight pink around apex which fades to white.

*Number of buds per spur.*—Average number 2, varies from 2 to 3.

Flowers:

*Size.*—Medium to large. Average height 14.6 mm. Average diameter 29.5 mm.

*Petals.*—Number 5, alternately arranged to sepals. Size — medium. Average length 13.5 mm. Average width 13.4 mm. Form — orbicular. Margin — sinuate. Both upper and lower surfaces glabrous. Color — N 9.5/ (white).

*Sepals.*—Number 5, alternately arranged to petals. Shape — ovate. Apex — rounded. Size — medium. Average length 4.5 mm. Average width 3.8 mm. Both upper and lower surfaces glabrous. Color — upper surface varies from 2.5GY 9/4 to 2.5Y 8/4. Lower surface varies from 7.5RP 4/2 to 7.5RP 3/8.

*Stamens.*—Average number per flower 31. Filament — average length 9.8 mm. Filament color N 9.5/ (white). Anther color varies 5Y 8.5/14 to 5Y 8/14.

*Pollen.*—Abundant, self sterile, pollinator required. Color varies from 2.5Y 8/12 to 2.5Y 7/12.

*Pistil.*—Normally 1, varies from 1 to 2. Surface — pubescent. Average length 14.1 mm. Average height of stigma as compared to stamens, 1.8 mm below anthers. Color varies from 10Y 9/6 to 10Y 8.5/6.

*Fragrance.*—Slight.

*Blooming period.*—Date of 1$^{st}$ Bloom Feb. 23, 2005. Date of Petal Fall Mar. 5, 2005, varies slightly with climatic conditions.

*Color.*—N 9.5/ (white).

*Number flowers per flower bud.*—Average 2, varies from 1 to 2.

*Pedicel.*—Average length 3.6 mm. Average width 1.1 mm. Color varies from 5GY 8/6 to 5GY 8/8.

Fruit:

*Maturity when described.*—Firm ripe.

*Date of 1st picking.*—Jun. 15, 2005.

*Date of last picking.*—Jun. 23, 2005, varies slightly with climatic conditions.

*Size.*—Medium. Average diameter axially 53.3 mm. Average transversely in suture plane 58.1 mm. Average across suture plane 53.7 mm. Average weight 113.6 grams, varies slightly with fertility of the soil, amount of thinning and climatic conditions.

*Form.*—Globose.

*Suture.*—Nearly smooth, extends from base to apex.

*Ventral surface.*—Nearly smooth, well sealed.

*Apex.*—Varies from rounded to slightly retuse.

*Base.*—Varies from flat to slightly retuse.

*Cavity.*—Rounded to slightly elongated in suture plane. Average depth 4.1 mm. Average diameter 9.5 mm.

Stem:

*Size.*—Small. Average length 6.3 mm. Average diameter 2.2 mm.

*Color.*—Varies from 2.5GY 7/8 to 2.5GY 6/8.

Flesh:

*Ripens.*—Evenly.

*Texture.*—Firm.

*Fibers.*—Few, small, tender.

*Firmness.*—Firm, with greater firmness than most commercial apricots.

*Aroma.*—Moderate.

*Amydgalin.*—Undetected.

*Eating quality.*—Very good.

*Flavor.*—Very good.

*Juice.*—Moderate, enhances flavor.

*Brix.*—Average 15.7°, varies slightly with amount of fruit per tree and climatic conditions.

*Color.*—Varies from 2.5Y 8/8 to 2.5Y 8/10. Pit cavity varies from 2.5Y 8/10 to 2.5Y 7/12.

Skin:

*Thickness.*—Medium.

*Surface.*—Smooth.

*Down.*—Moderate amount, very short in length.

*Tendency to crack.*—None.

*Color.*—Ground color varies from 10YR 8/10 to 2.5Y 8/10. Overspread color varies from 5R 4/12 to 7.5R 4/10 on approximately 30% of surface area.

*Tenacity.*—Tenacious to the flesh.

*Astringency.*—None.

Stone:

*Type.*—Semi-freestone.

*Size.*—Medium to large. Average length 24.8 mm. Average width 21.8 mm. Average thickness 13.0 mm.

*Form.*—Ovoid.

*Base.*—Usually flat, varies from flat to slightly concave.

*Apex.*—Very slightly pointed. Average length 0.2 mm.

*Surface.*—Slightly pitted throughout. Two narrow furrows on each side of suture extending from base to apex.

*Sides.*—Unequal, one side extending further from suture plane.

*Ridges.*—One small, narrow ridge bordering the furrow near the suture.

*Tendency to split.*—None.

*Color.*—Varies from 7.5YR 7/4 to 10YR 7/6 when dry.

Kernal:

*Form.*—Ovoid.

*Size.*—Medium. Average length 14.8 mm. Average width 11.3 mm. Average depth 6.6 mm.

*Viability.*—Viable, complete embryo development.

*Skin color.*—Varies from 10YR 8/6 to 2.5Y 8/6, when dry.

Use: Dessert. Market — local and long distance.

Keeping quality: Good, held firm in cold storage 2 weeks at 38° to 42° F. without internal breakdown or appreciable loss of flavor.

Shipping quality: Good, minimal bruising of flesh or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit diseases resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, semi-vigorous growth and being a productive and regular bearer of medium size, semi freestone fruit with very good flavor and eating quality; the fruit is further characterized by having skin with an attractive orange red blush over approximately 30% of a high yellow ground color, holding firm on the tree 8 to 10 days after maturity (shipping ripe) and in comparison to its interspecific proprietary maternal parent (38GH47), which has fruit with smooth slick skin surface, the fruit of the new variety has pubescence and is approximately 24 days earlier in maturity.

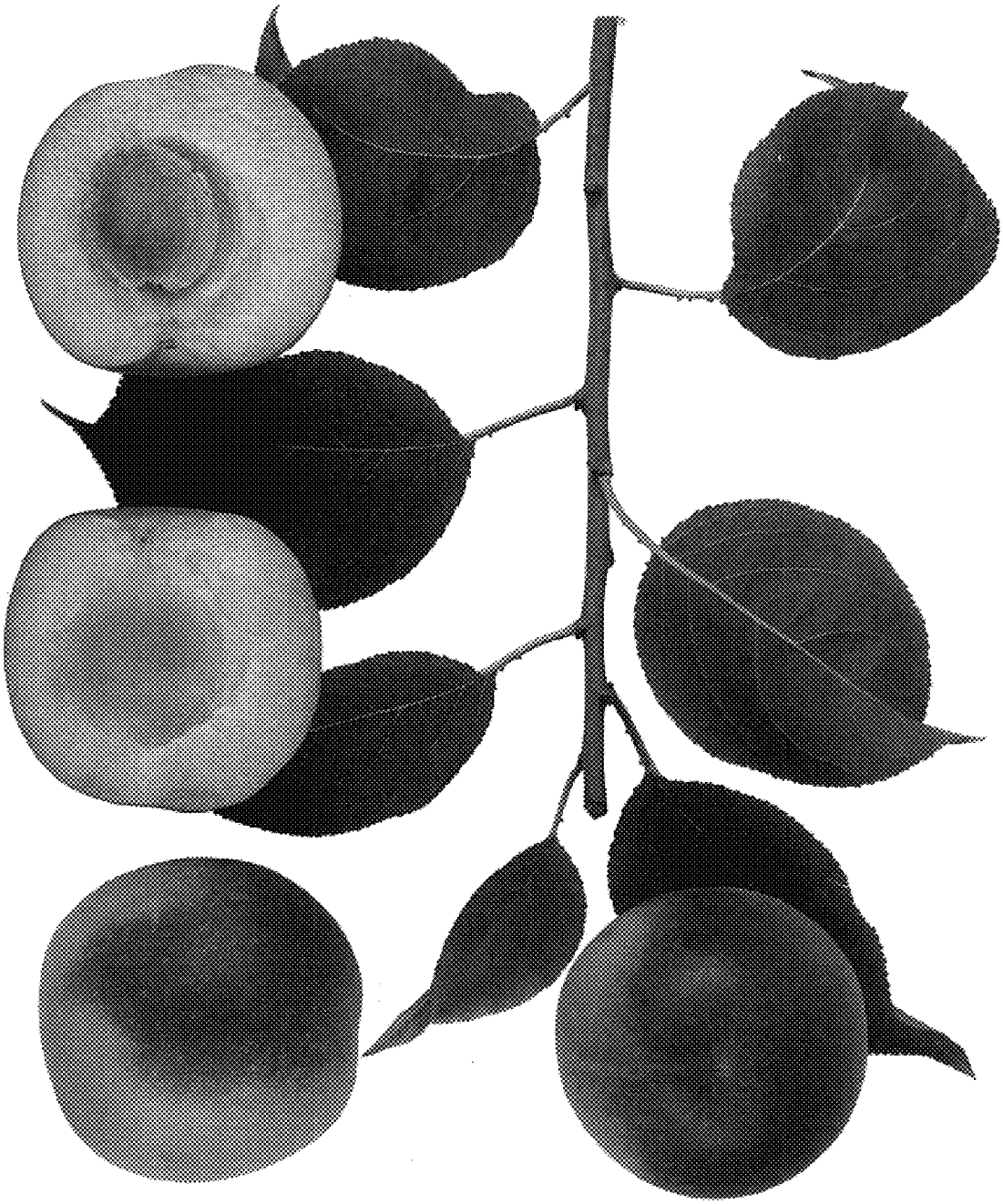

* * * * *